United States Patent [19]

Quang et al.

[11] Patent Number: 5,026,459

[45] Date of Patent: * Jun. 25, 1991

[54] APPARATUS FOR REACTIVE DISTILLATION

[75] Inventors: Dang Vu Quang, Neuilly; Pierre Amigues, Francheville; Jean-Ferdinand Gaillard, Lyon, all of France

[73] Assignees: Institut Francais Du Petrole, Rueil-Malmaison; Elf France, Courbevoie, both of France

[*] Notice: The portion of the term of this patent subsequent to May 7, 2008 has been disclaimed.

[21] Appl. No.: 356,087

[22] Filed: May 24, 1989

Related U.S. Application Data

[62] Division of Ser. No. 171,339, Mar. 21, 1988, Pat. No. 4,847,431.

[51] Int. Cl.$^5$ .............................. B01D 3/20; B01J 8/04
[52] U.S. Cl. ..................................... 202/158; 203/29; 203/DIG. 6; 261/97; 422/193; 422/194; 422/195; 568/699
[58] Field of Search ...................... 203/DIG. 6, 28, 99, 203/1, 29; 202/158; 568/699; 422/193, 194, 187, 191, 195; 261/96, 97

[56] References Cited

U.S. PATENT DOCUMENTS

| | | | |
|---|---|---|---|
| 2,555,606 | 6/1951 | Potts | 203/DIG. 6 |
| 2,826,601 | 3/1958 | Barsky | 203/DIG. 6 |
| 3,241,926 | 3/1966 | Parker et al. | 203/DIG. 6 |
| 3,579,309 | 5/1971 | Sennewald et al. | 203/DIG. 6 |
| 3,629,478 | 12/1971 | Haunschild | 203/DIG. 6 |
| 4,089,752 | 5/1978 | Hancock | 203/DIG. 6 |
| 4,314,972 | 2/1982 | Nakane et al. | 422/195 |
| 4,471,154 | 9/1984 | Franklin | 203/DIG. 6 |
| 4,475,005 | 10/1984 | Paret | 568/699 |
| 4,808,350 | 2/1989 | Robbins et al. | 261/97 |
| 4,836,989 | 6/1989 | Aly et al. | 261/97 |

Primary Examiner—Wilbur Bascomb
Attorney, Agent, or Firm—Millen, White & Zelano

[57] ABSTRACT

The invention concerns a process and apparatus for manufacturing methyl tert-butyl ether (MTBE) by reacting methanol with an isobutene-containing hydrocarbon mixture.

This process is characterized by the steps of:
introducing the reactants into a reaction-distillation zone containing at least two superposed and non-contiguous fixed beds (2a, 2b) of catalyst of the sulfonated resin type, wherein passageways are provided for a vapor phase, at least one distillation tray (4a), at least one liquid redistribution tray (5),
maintaining distillation conditions in the zone so as to have a descending liquid phase and an ascending vapor phase,
maintaining a continuous liquid phase in the lower part of the beds,
discharging a vapor phase containing a high proportion of unconverted hydrocarbons from the top (8) of the zone, and
withdrawing a liquid phase of high MTBE content from the bottom (10) of the zone.

9 Claims, 2 Drawing Sheets

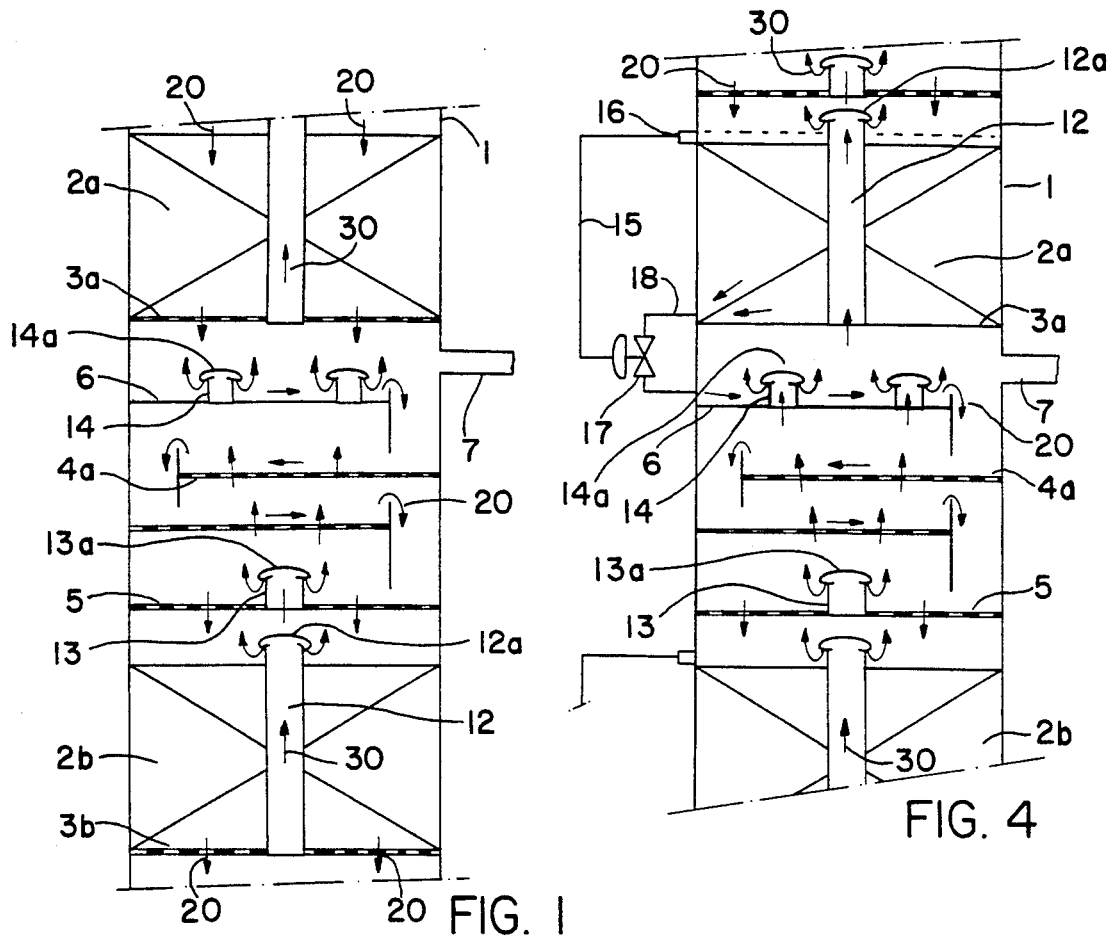
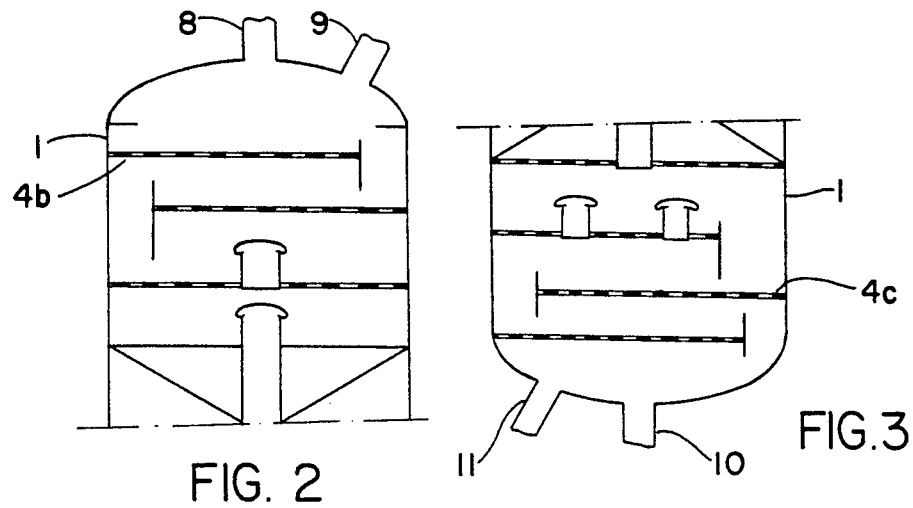

APPARATUS FOR REACTIVE DISTILLATION

This is a division of U.S. application Ser. No. 07/171,339 filed March 21, 1988, now U.S. Pat. No. 4,847,431.

The present invention relates to a process for manufacturing a tertiary alkyl ether by reacting an aliphatic alcohol with a hydrocarbon mixture containing at least one iso-olefin.

It also concerns an apparatus for carrying out said process.

The present invention more particularly concerns the manufacture of methyl tert-butyl ether (MTBE) from isobutene and methanol, the manufacture of tert-amyl methyl ether (TAME) from isopentene and methanol and the manufacture of MTBE and TAME from isobutene, isopentene and methanol.

BACKGROUND OF THE INVENTION

Tertiary alkyl ethers, particularly methyl tert-butyl ether (MTBE) and tert-amyl methyl ether (TAME), are of high interest for improving gasoline qualities, particularly in view of their anti-knock properties.

It is known to manufacture tertiary alkyl ethers, particularly methyl tert-butyl ether (MTBE) and tert-amyl methyl ether (TAME) which are the most conventional ethers, by reacting an iso-olefin, generally contained in a hydrocarbon fraction, with an aliphatic alcohol, for example methanol, in the presence of an acid catalyst, for example sulfuric acid, hydrofluoric acid, aluminum chloride or boron fluoride, or in the presence of carbonaceous materials containing -$SO_3H$, for example sulfonated coals, sulfonated phenol-formaldehyde resins, sulfonated coumarone-idene polymers or preferably sulfonated polystyrene-divinylbenzene resins.

It has been known for a long time that the reaction between methanol and tertiary olefins is a balanced reaction, and therefore it is difficult to obtain acceptable conversion rates of iso-olefins without using a very high methanol excess with respect to the stoichiometrical amount; however, methanol forms azeotropes with the light hydrocarbons complicating its recovery by conventional methods such as, for example, azeotropic distillation combined with recycling to the reactor, as disclosed in the French patent 2 411 881. U.S. Pat. No. 4,204,077 teaches methanol recovery by extraction with a solvent such as ethylene glycol. However these methods require costly investment and are complex in operation (due to the necessary use of several reactors and distillation columns to produce and separate the tertiary alkyl ether).

A method has thus been proposed for converting a major part of the iso-olefins without necessarily using a methanol excess : it consists of the reactive distillation (or catalytic distillation) method, according to which the etherification reaction with the catalyst and the distillation for separating the tertiary alkyl ether, as it is formed, from the other unconverted constituents, are performed in the same enclosure (U.S. Pat. No. 3,629,478, EP-B 8 860, FR 2 503 700).

The European patent 8 860 proposes to use a distillation column, filled with a catalyst convenient for producing methyl tert-butyl ether (MTBE) wherein the catalyst also acts as packing for the distillation, thus forming MTBE and simultaneously separating $C_4$ constituents. Although the process disclosed in this patent represents substantial progress in the field of reactive distillation, the contact between the liquid phase and the catalyst seems to be more or less intermittent, due to the disturbing effect of the vapor phase.

French patent 2 503 700 proposes the use of a series of catalytic steps with ascending vapor-liquid flow through each catalyst bed with the catalyst being embedded. But the distillation effect is not as important as expected. Moreover, a hydrodynamic problem may arise : As a matter of fact, in view of the gravity effect, it will not be easy for the liquid to flow upwardly through each catalyst bed.

U.S. Pat. No. 3,629,478, which represents the closest prior art, discloses the use of distillation trays and the placement of the catalyst in bulk (i.e., freely) only in the downcomers of said distillation trays, in order to avoid the disturbing effect of the vapor phase through the catalyst. However, the presence of catalyst in such downcomers generates such a pressure drop that the liquid preferably flows down counter-currently through the orifices provided for the vapor on the working table of each distillation tray, instead of passing through the catalyst bed which is thus bypassed.

SUMMARY OF THE INVENTION

The present invention copes with the above-mentioned disadvantages: as a matter of fact, by means of devices which form integral parts of the invention, the distillation liquid is compelled to pass over different catalyst beds contained in the distillation-reaction zone, i.e, a zone defined by an enclosure where are conducted the reaction and/or the distillation. Its residence time through said catalyst beds is controlled and the contact between the catalyst and the vapor phase is avoided by the provision of passageways reserved for the latter through said catalyst beds. Thus, in particular, as a result of a very good distillation effect, very satisfactory yields of tertiary alkyl ether are obtained.

BRIEF DESCRIPTION OF THE DRAWINGS

The invention will be now described in more detail by way of illustrative and non-limiting examples, with reference to the accompanying drawings wherein :

FIGS. 1, 2 and 3, respectively illustrate the middle, the top and the bottom parts of an enclosure according to a preferred embodiment of the invention (where, in particular, the hereinafter defined support members or bottoms are perforated), FIG. 4 illustrates the middle part of an enclosure corresponding to another embodiment of the invention (where, in particular, said support members or bottoms are not perforated but are tight).

DETAILED DESCRIPTION OF THE DRAWINGS

Figure 4A:
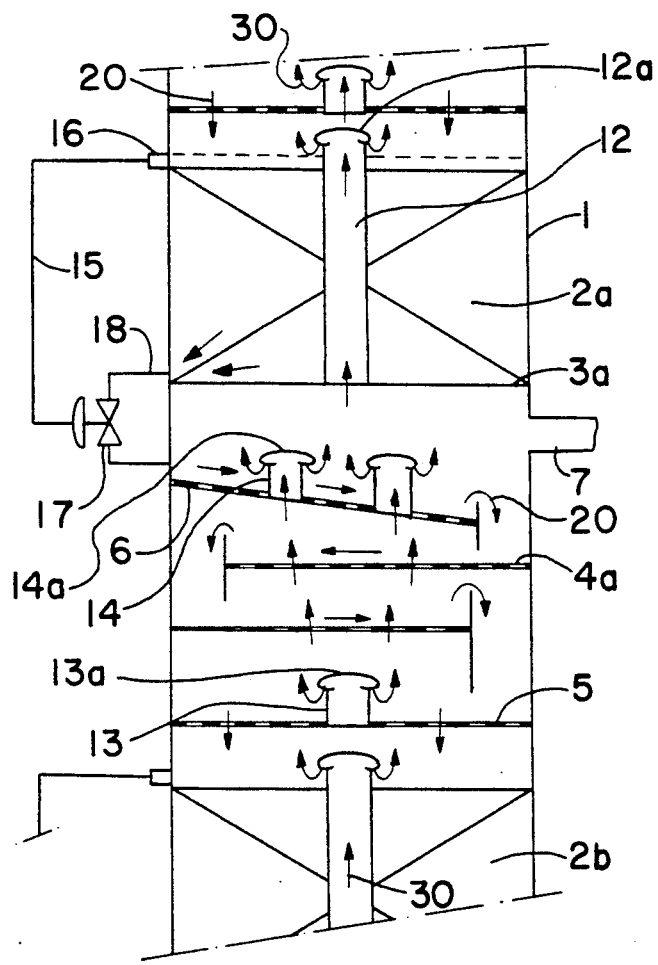
FIG. 4a illustrates an embodiment identical to that of FIG. 4 except that the liquid distribution tray is inclined.

The present invention has object of the present invention is to provide an apparatus process for manufacturing a tertiary alkyl ether (or several tertiary alkyl ethers) by reacting an aliphatic alcohol with a hydrocarbon mixture containing at least one iso-olefin in a reaction-distillation zone (i.e., a zone where are performed the reaction and/or the distillation), defined (see FIGS. 1, 2, 3) by an enclosure (1) of substantially cylindrical shape, for example, vertical, containing at least one catalyst of the sulfonated resin type, for example, a sulfonated polystyrene-divinylbenzene resin, said process being characterized by the steps of:

i —introducing the reactant charge containing at least said alcohol and at least said hydrocarbon mixture into said reaction-distillation zone which contains :

a) at least two superposed and non-contiguous fixed beds (2a, 2b) of said catalyst of sulfonated resin type, each of said beds being placed on a support member or bottom (3a, 3b), each catalyst bed and each corresponding support member (or bottom) being traversed by at least one catalyst-free passageway for a vapor phase (for example a funnel or duct (12) whose upper end is preferably protruding, i.e, rises above the top of said catalyst bed, said upper end being preferably covered, (e.g. cap 12a), but not closed, thus preventing the liquid present in said bed from being discharged in said funnel, said passageway being located/ for example, in the central part of the catalyst beds (the catalyst beds may have different thicknesses), (b) at least one catalyst-free distillation tray (4a), placed in at least one free space between two consecutive catalyst beds (2a, 2b), (c) at least one catalyst-free discontinuous tray (i.e., provided with a plurality of discontinuities) for liquid redistribution (5), placed in at least one free space between a distillation tray and the catalyst bed just below said distillation tray, each discontinuous liquid redistribution tray being further provided with at least one catalyst-free passageway for a vapor phase (for example, a funnel or duct (13) whose upper end is preferably protruding, i.e., rises above the bottom of said liquid redistribution tray, said upper end being preferably covered (e.g. cap 13a) (but not closed), thus preventing the discharge of liquid present on said plate into said funnel), for example, located in the central of the redistribution tray part, ii —maintaining the distillation conditions in said reaction-distillation zone, so as to obtain a liquid phase and a vapor phase in said zone, iii —downwardly circulating the liquid phase through said catalyst beds (2a, 2b), said distillation tray(s) (4a), and said discontinuous liquid redistribution tray(s) (5), iv —maintaining a continuous liquid phase at least in the lower part of each catalyst bed by controlling the liquid level in each of said beds, thus controlling the resistance to the liquid flow at the bottom of each of said beds, v —upwardly circulating the vapor phase through said free passageway(s) (e.g. duct 12) of said catalyst beds (2a, 2b) (thus avoiding generation of pressure drops), through said free passageways (e.g., duct 13) of said discontinuous liquid redistribution tray(s) (5) and said, distillation tray(s) (4a) (this ascending vapor phase not being in contact with the catalyst in each of said catalyst beds), vi —discharging from the top (8) of the reaction-distillation zone a vapor phase mainly containing unconverted hydrocarbons, vii —withdrawing from the bottom (10) of the reaction-distillation zone a liquid phase mainly containing said tertiary alkyl ether(s).

The discontinuities of each liquid redistribution tray (5) are orifices for the passage of the liquid phase, regularly distributed so as to uniformly spray liquid on the catalyst bed just below each liquid redistribution tray.

Each of the distillation trays used according to the present invention comprises :

at least one discontinuous plate (i.e., provided with discontinuities for the passage of the vapor phase), to provide stirring and mixing of liquid and vapor flows, at least one downcomer (or gutter), placed, for example, at the edge of each distillation tray, for liquid conditioning and control of its flow regularity (downcomer wherethrough will flow the liquid previously present on the plate of said tray), and at least one overflow (or small lip) edging each downcomer, destined to maintain a certain liquid level on the plate of said tray and hence to control the regularity of liquid flow discharge from said plate.

These distillation trays may be selected from those known in the art, particularly sieve trays, bubble-cap trays, valve trays, but any other distillation device of the art, such as an inert packing or an assembly of inert packings (provided with a support member), may optionally be used instead of a distillation tray.

According to a preferred embodiment of the invention, the liquid level of each catalyst bed, hence the contact (liquid-catalyst) and reaction time is controlled by means, i.e, by the selection,of regularly distributed perforations in each corresponding support member or bottom (3a, 3b), perforations wherethrough flows the liquid contained in each catalyst bed. Thus, a continuous liquid phase may be maintained in each catalyst bed (2a, 2b) while providing, owing to each perforated support member or bottom (3a, 3b), for a substantially constant downward flow through the reaction-distillation zone. The smaller the total cross-sectional area of the perforations of a perforated bottom, the higher the height of the continuous liquid phase inside the corresponding bed. The lower the running rate, the lower the liquid height inside each catalyst bed.

In the preceding preferred embodiment of the invention, each free space between a distillation tray and the catalyst bed just said distillation tray may be provided (see for example FIG. 1) with a catalyst-free liquid distribution tray (6), optionally inclined (see FIG. 4a), traversed by at least one duct or funnel (14) for the passage of the vapor phase (duct or funnel whose upper end is preferably protruding, i.e., raises above the tray bottom, said end being optionally covered by a cap (14a) (but not closed), thus preventing the liquid from being discharged through said duct or funnel). Each liquid distribution tray (6) is further provided at one end, for example at its lowermost end when it is substantially inclined (FIG. 4a), with at least one free passageway (consisting preferably of a discharge duct or downcomer edged with an overflow) for the liquid phase. Each liquid distribution tray is so placed that, after previous passage over said liquid distribution tray (6), the liquid phase is supplied to a distillation tray just below said liquid distribution tray, at the most remote place from the overflow thereof, i.e., at the opposite side of said overflow. The liquid flow on the plate of said distillation tray is thus more regular and the distillation on said tray still more efficient.

According to another preferred embodiment of the invention (see FIG. 4 or 4a , by way of example), the liquid level in each catalyst bed (2a, 2b) (and hence the resistance to liquid flow at the bottom of each bed) is controlled by the use of a corresponding impermeable (not perforated) support member or bottom (3a, 3b) whereon is laid said bed,and of at least one discharge duct (18) wherethrough the liquid can flow from the bottom of said bed to an adjacent part of said enclosure, said duqt being equipped with a control valve (17) monitored (via line 15) through a controller (16) which senses the level of liquid in said catalyst bed (said controller being, for example, placed at the upper part of said bed).

In this preferred embodiment the liquid level in each catalyst bed and the corresponding reaction times, may be controlled, irrespective of the liquid flow rate and/or the running rate of the unit where the process is operated. As a matter of fact, it is known that a minimum contact time between the reactants and the catalyst is necessary for converting the iso-olefin and the aliphatic alcohol. But too long of a contact time will tend to favor secondary reactions such as, for example, olefin dimerization or oligomerization. Thus, the involved monitoring provides for an optimum yield and conversion selectivity.

Advantageously, at least a part of the vapor phase discharged from the top (8) of the reaction-distillation zone may be condensed (in a condenser external to enclosure (1) defining said zone, not shown in the figures) then fed back to said zone, for example towards the top thereof, as liquid flow, called reflux.

Similarly, at least a part of the liquid phase withdrawn from the bottom (10) of the reaction-distillation zone may be vaporized ( by passage through a reboiler external to enclosure (1), not shown in the figures), then reintroduced into said zone, for example at the bottom thereof, as vapor flow, called reboiling vapor.

The catalyst may be of any adequate shape, particularly a substantially cylindrical or a substantially spherical shape.

In each catalyst bed the catalyst may be enclosed in one or several coverings permeable to liquid but impermeable to catalyst particles (i.e., retaining said catalyst solid particles), coverings made for example of a fabric cloth or a cloth of intercrossed, mainly metallic wires.

The catalyst may on the contrary be laid in bulk, i.e freely, inside each catalyst bed. According to an improved embodiment of the invention, the liquid flowing from the lowermost catalyst bed of the reaction-distillation zone is then collected, withdrawn, filtered in at least one filtering device (external to enclosure (1)) and then reintroduced into the reaction-distillation zone between the level at which it has been withdrawn and the bottom of said zone, optionally on a distillation tray just below the lowermost catalyst bed of said zone. By this filtering all the catalyst fragments, if any, can be driven away by the liquid phase, thus preventing the plugging of the enclosure bottom by accumulation thereof.

The space between the top of the reaction-distillation zone (i.e., the top of the enclosure) and the uppermost catalyst bed of said zone (see FIG. 2) may preferably contain at least one catalyst-free distillation tray (4b).

The space between the bottom of the reaction-distillation zone (the bottom of the enclosure) and the lowermost catalyst bed of said zone (see FIG. 3), may also preferably contain at least one catalyst-free distillation tray (4c).

According to another preferred embodiment of the invention (see FIG. 1, 4 or 4a), the charge of reactants, containing at least one aliphatic alcohol and at least one hydrocarbon mixture, is introduced into the reaction-distillation zone at a level (7) thereof, below at least one catalyst bed and more preferably such that the lowermost catalyst bed of said zone be above said level.

According to an improved embodiment of the invention, it may be possible, in addition to the charge, to introduce said alcohol separately (i.e., alone) into the reaction-distillation zone, through at least one inlet different from that of said charge and preferably located at the top of at least one catalyst bed and, more preferably, at the top of each catalyst bed. This alcohol complementary amount, which favors the etherification reaction (resulting in the reduction of dimer formation, if any) is then almost completely consumed as it is introduced and is found only in a small amount in the vapor phase where a too high alcohol amount could disturb the separation of tertiary alkyl ether(s) from hydrocarbons.

This improvement (alcohol introduction at the top of at least one catalyst bed, preferentially at the top of each catalyst bed) is particularly interesting when the charge contains, in addition to said aliphatic alcohol and to said hydrocarbon mixture, a substantial amount of corresponding tertiary alkyl ether(s).

The alcohol is preferably introduced at a temperature lower than its boiling temperature.

The reflux ratio (i.e., a ratio between the reflux liquid and the withdrawn liquid),in proportion to the distillate, is generally maintained in the range from 0.1:1 to 20:1; preferably from 0.5:1 to 5:1. The operation is mostly conducted inside enclosure (1) within a relatively wide pressure and temperature range: for example, a pressure of 1-30 bars (100-3, 000 kPa), preferably 2-20 bars (200 -2, 000 kPa) and a temperature from 10 to 200° C., preferably from 40 to 160° C., in the whole enclosure.

Each of the catalyst beds used according to the invention fills the whole circular section of the reaction-distillation zone, i.e., the whole circular section of enclosure (1).

In FIGS. 1, 4 and 4a, given by way of example, the liquid phase preferentially follows the path indicated by arrows 20 and the vapor phase preferentially follows the path indicated by arrows 30.

As it flows downwardly through the reaction-distillation zone, the liquid phase progressively increases its content of tertiary alkyl ether, which is less volatile than the alcohol and the still unreacted iso-olefin, and than the other nonetherifiable constituents of the hydrocarbon mixture. Thus, the liquid phase of withdrawn from the bottom of the reaction-distillation zone mainly contains tertiary alkyl ether. The catalyst beds according to the invention operate almost exclusively in liquid phase : accordingly they have a very high efficiency.

The presence of alcohol on the distillation trays is also substantially reduced to a minimum and the vapor phase discharged from the top (8) of the reaction-distillation zone does not contain more than traces of uncoverted alcohol.

Another object of the present invention is to provde (see FIGS. 1, 2 and 3) an apparatus or vessel (1) substantially of cylindrical shape, comprising at least one line (7) for introducing a charge, at least one line (8), at the top of said vessel, for withdrawing a vapor phase, at least one line (9), in the vicinity of the top of said vessel, for a reflux feed, at least one line (10), at the bottom of said vessel, for withdrawing a liquid phase, at least one line (11), in the vicinity of the bottom of said vessel for introducing an at least partly vaporized phase, said vessel being characterized in that it contains :

(a) at least two superposed and non-contiguous fixed catalyst beds (2a, 2b) (each of said beds being placed on a perforated support member or bottom (3a, 3b), each bed and each corresponding support member being traversed, for example in their central part, by at least one funnel or duct) (12) preferably filling the whole internal circular section of the vessel (1).

(b) at least one distillation tray, provided in at least one free space between two consecutive catalyst beds (2a, 2b), and (c) at least one discontinuous tray (5) (provided with a plurality of discontinuities), for liquid redistribution, located in at least one free space between a distillation tray and the catalyst bed just below it, each discontinuous liquid redistribution tray being further provided with at least one funnel or duct (13) (whose upper end is preferably protruding, i.e., raises above the bottom of said liquid redistribution tray, said end being preferably covered, but not closed, by a cap) (13a), for example, in its central part.

It is also possible, instead of at least one distillation tray, to use any other distillation device known in the art, particularly an inert packing or packing assembly (provided with a support member).

The apparatus (1) according to the invention may also contain at least one device selected from:

at least one distillation tray (4b), between the top of the vessel and the uppermost catalyst bed therein, and at least one distillation tray (4c) between the bottom of the vessel and the lowermost catalyst bed therein.

The apparatus (1) according to the invention may further comprise, in each free space between a distillation tray and the catalyst bed just above said tray, a liquid distribution tray (6), optionally inclined (see FIG. 4a), wherethrough passes at least one duct or funnel (14) (whose upper end is preferably protruding and preferably covered by a cap (14a) ) and provided at one end, e.g., at its lowermost end when it is substantially inclined, with at least one free passageway (preferably consisting, for example, of a discharge duct edged with an overflow).

This apparatus is adapted for carrying out the process according to the invention.

The apparatus may be used, for example, for manufacturing methyl tert-butyl ether (MTBE) from methanol and isobutene, for manufacturing tert-amyl methyl ether (TAME) from methanol and isopentene and for manufacturing MTBE and TAME from methanol, isobutene and isopentene, in the presence of a convenient catalyst such as a catalyst of sulfonated resin type (for example, a sulfonated polystyrene-divinylbenzene resin), these types of use being not limitative.

EXAMPLE (comparative)

A charge, formed of methanol and of a mixture of butenes and butanes containing about 25% of isobutene, already converted to MTBE, in a proportion of 75% over a bed of sulfonated resin catalyst, is introduced into an enclosure containing a plurality of beds of said catalyst and of distillation trays :

according to the process of the invention (operating pressure of about 9 bars, temperature ranging from about 65 to 150° C. and reflux ratio of about 1:1) about 80% of the residual isobutene may then be converted to MTBE in said enclosure, in particular by placing a distillation tray in each space between two consecutive catalyst beds(beds provided with a funnel).

It is observed that, for the same results, the number of said catalyst beds used in the process of the invention is one-half of the number of such beds (not provided with a funnel) required in a conventional catalytic column.

What is claimed as the invention is:

1. An apparatus for reactive distillation comprising:

a substantially cylindrical vessel having an upper portion and a lower portion, at least one feed inlet means for introducing a charge, at least one vapor outlet means in said upper portion of said vessel for withdrawing a vapor phase, at least one reflux inlet means in said upper portion of said vessel for a reflux feed, at least one liquid outlet means in said lower portion of said vessel for withdrawing a liquid phase, at least one vapor inlet means in said lower portion of said vessel for introducing an at least partially vaporized phase;

at least two superposed non-contiguous fixed catalyst beds positioned within said vessel, each of said beds being placed on a perforated support member, each bed and each corresponding support member being traversed by at least one funnel;

at least one distillation tray placed in at least one free space between two consecutive beds; and at least one discontinuous liquid redistribution tray placed in at least one free space between a distillation tray and the catalyst bed just below said distillation tray, each discontinuous liquid redistribution tray being further provided with at least one duct for passage of an upwardly flowing vapor stream wherein said catalyst bed, distillation tray, and redistribution tray are positioned to direct a downwardly flowing liquid discharged from said distillation tray onto and through said redistribution tray and then to flow downwardly through said catalyst bed.

2. An apparatus according to claim 1, further comprising at least one distillation tray placed in said upper portion of said vessel above the uppermost catalyst bed of the apparatus.

3. A process according to claim 1, further comprising at least one distillation tray placed in said lower portion of said vessel below the lowermost catalyst bed of the apparatus.

4. A process according to claim 1, further comprising a liquid distribution tray, traversed by at least one funnel, provided at one end with at least one passageway, and placed in each free space between a distillation tray and the catalyst bed just above said distillation tray.

5. A process according to claim 4, wherein the liquid distribution tray is inclined.

6. A process according to claim 2, further comprising at least one distillation tray placed in said lower portion of said vessel below the lowermost catalyst bed of the apparatus.

7. A process according to claim 2, further comprising a liquid distribution tray, traversed by at least one funnel, provided at one end with at least one passageway, and placed in each free space between a distillation tray and the catalyst bed just above said distillation tray.

8. A process according to claim 3, further comprising a liquid distribution tray, traversed by at least one funnel, provided at one end with at least one passageway, and placed in each free space between a distillation tray and the catalyst bed just above said distillation tray.

9. A process according to claim 7, further comprising at least one distillation tray placed in said lower portion of said vessel below the lowermost catalyst bed of the apparatus.

* * * * *

UNITED STATES PATENT AND TRADEMARK OFFICE
CERTIFICATE OF CORRECTION

PATENT NO. : 5,026,459

DATED : June 25, 1991

INVENTOR(S) : Quang et al.

It is certified that error appears in the above-identified patent and that said Letters Patent is hereby corrected as shown below:

On the title page,

Under related U.S. Application Data - - - second line reads 4,847,431 should read - -  4,847,430

Signed and Sealed this

Thirteenth Day of October, 1992

*Attest:*

DOUGLAS B. COMER

*Attesting Officer*     *Acting Commissioner of Patents and Trademarks*